(12) United States Patent
Langrana et al.

(10) Patent No.: US 8,729,246 B2
(45) Date of Patent: May 20, 2014

(54) AGENT DELIVERY SYSTEM CAPABLE OF SELECTIVELY RELEASING AN AGENT

(75) Inventors: Noshir A. Langrana, West Windsor, NJ (US); David C. Lin, East Windsor, NJ (US); Bernard Yurke, Boise, ID (US)

(73) Assignees: Alcatel Lucent, Paris (FR); Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 13/571,916

(22) Filed: Aug. 10, 2012

(65) Prior Publication Data

US 2013/0202582 A1 Aug. 8, 2013

Related U.S. Application Data

(62) Division of application No. 10/260,243, filed on Sep. 30, 2002, now Pat. No. 8,389,700.

(51) Int. Cl.
*C07H 21/02* (2006.01)

(52) U.S. Cl.
USPC ..................................... 536/23.1

(58) Field of Classification Search
None
See application file for complete search history.

(56) References Cited

U.S. PATENT DOCUMENTS 7,919,600 B2 * 4/2011 Mills et al. .................. 536/22.1
8,389,700 B2 * 3/2013 Langrana et al. ............ 536/23.1

* cited by examiner

*Primary Examiner* — Scott Long
(74) *Attorney, Agent, or Firm* — Hitt Gaines, P.C.

(57) ABSTRACT

The present invention provides a composition for selectively delivering an active agent to a portion of an organism. The composition comprises first and second polymer portions, having first and second functional groups attached as a side-chain thereto, respectively. The first and second functional groups form cross-links between the first and second polymer portions. The cross-links are capable of being broken by a substance of the organism, thereby resulting in release of the active agent. The composition provides a novel means for controlling the selective release of the active agent in the organism.

12 Claims, 9 Drawing Sheets

AGENT DELIVERY SYSTEM CAPABLE OF SELECTIVELY RELEASING AN AGENT

CROSS-REFERENCE TO RELATED APPLICATION

This Application is a Divisional of U.S. application Ser. No. 10/260,243 filed on Sep. 30, 2002 now U.S. Pat. No. 8,389,700 to Noshir A. Langrana et al., entitled "AN AGENT DELIVERY SYSTEM CAPABLE OF SELECTIVELY RELEASING AN AGENT," currently Allowed; commonly assigned with the present invention and incorporated herein by reference.

This application is related to the disclosure of U.S. application Ser. No. 10/252,287 entitled, "COMPOSITIONS THAT REVERSIBLY GEL AND DE-GEL," to Allen P. Mills and Bernard Yurke ("Mills"), filed on Sep. 23, 2002 which has issued as U.S. Pat. No. 7,919,600 on Apr. 5, 2011, commonly assigned with the present invention, and incorporated by reference as if reproduced herein in its entirety.

TECHNICAL FIELD OF THE INVENTION

The present invention is directed, in general, to a composition for delivering a biologically active agent.

BACKGROUND OF THE INVENTION

Compositions are used extensively in a wide range of biomedical applications, for the delivery of diagnostic or therapeutic active agents. A longstanding problem in the manufacture of such compositions is the controlled delivery of the active agents to particular organisms or sites within organisms, such as a particular cell type. The timed release of active agents from such compositions, also remains problematic. These problems reside in part due to the manner in which such active agents are released from the composition.

Polymers may be cross-linked to form compositions that serve as a matrix or reservoir for delivery of a drug over a sustained period. For example, cross-linked hydrogels of polyacrylamide, are capable of absorbing a substantial amount of water to form elastic or inelastic compositions. The compositions may absorb water and swell to thereby release the drug incorporated therein. Unfortunately, the hydrogels may have a number of undesirable characteristics.

For example, some such compositions are not biodegradable. Therefore, the removal of the compositions from an organism requires excretion of the composition. Other compositions require the use of undesirable solvents or monomers during manufacture. For instance, a conventional manufacture of polyacrylamide uses the monomer acrylamide and cross-linker N,N'methylbisacryamide. Residual amounts of the unreacted monomer and cross-linker typically remain in the final composition and can cause damage in surrounding tissues or inactivation of the active agent incorporated into the composition. Moreover, the preparation of such compositions may preclude inclusion of the active agent during formation of the matrix. For example, the conventional preparation of a polyacrylamide gel involves formation of a free radical on the growing polymer chain and cross-linking chains. Such a process could chemically alter and inactivate an active agent present during the gel's formation. Therefore, additional processing steps are typically taken to first prepare a capsule and then add the active agent to the capsule, usually along with waxes, fats or other fillers, to help the capsule maintain its shape. Furthermore, because the release of the active agent from certain gels is governed by diffusion, release is not targeted to a particular area of the body of an organism.

Accordingly, one objective of the invention is a process for making a composition capable of forming a gel in the presence of an active agent without deleteriously effecting the active agent. Another objective of the invention is a composition that enables a targeted release of an active agent included therein.

SUMMARY OF THE INVENTION

To address the above-discussed deficiencies, one embodiment of the present invention provides a composition comprising a first polymer portion having first functional groups attached as side-chains thereto and a second polymer portion having second functional groups attached as side-chains thereto. The first and said second functional groups are capable of forming cross-links between the first and second polymer portions. An active agent is disposed between the first and second polymer portions. The active agent is capable of being released by an interaction of a substance with the first or second polymer portions.

In another embodiment, the invention further provides a method for delivering an active agent to an organism. The method includes introducing a composition into an organism. The composition comprises a first and second polymer portion and an active agent as described above. The organism includes a substance capable of releasing the active agent from said composition by breaking the cross-links between first and second polymer portions.

BRIEF DESCRIPTION OF THE DRAWINGS

The invention is best understood from the following detailed description, when read with the accompanying FIGUREs. Various features may not be drawn to scale and may be arbitrarily increased or reduced for clarity of discussion. Reference is now made to the following descriptions taken in conjunction with the accompanying drawings, in which.

DETAILED DESCRIPTION

The present invention recognizes the advantageous use of an active agent delivery system that includes a composition of the present invention. The composition has functional groups, attached as side-chains to a polymer portions, so as to dispose or contain an active agent in the composition. Such compositions may be reversibly changed from a fluid to a solid gel state by cross-linking the polymers, as facilitated by interactions between the functional groups. The solid gel state is achieved without changes in temperature, the generation of undesirable free radicals or other intermediary chemicals. Thus, such compositions may be advantageously used as materials for the delivery of active agents to organisms.

The present invention further recognizes that the release of an active agent may be controlled by a substance that breaks the cross-links of the gel, for example, by cleaving one or more of the functional groups. When the substance is an enzyme, in addition to facilitating the release of the active agent, the enzymatic cleavage of the crosslinking functional groups facilitates the removal of the delivery system from the organism. Moreover, the delivery system may be used to advantageously target the release of the active agent, to a particular location in the organism, thereby reducing potential systemic side-effects associated with a non-targeted release of the active agent.

Preferably, the cross-link is formed by a plurality of reversible cross-links, such as hydrogen bonds, between the first and second functional groups. By forming the cross-link, the active agent is contained within the composition. Containment may be achieved by physically restricting the active agent within the internal structure of the composition, by chemical interactions between the active agent and the composition or a combination of both. Alternatively, as further illustrated below, the active agent may comprise a portion of the functional groups attached as side-chains to the first or second polymer.

Figure 1:
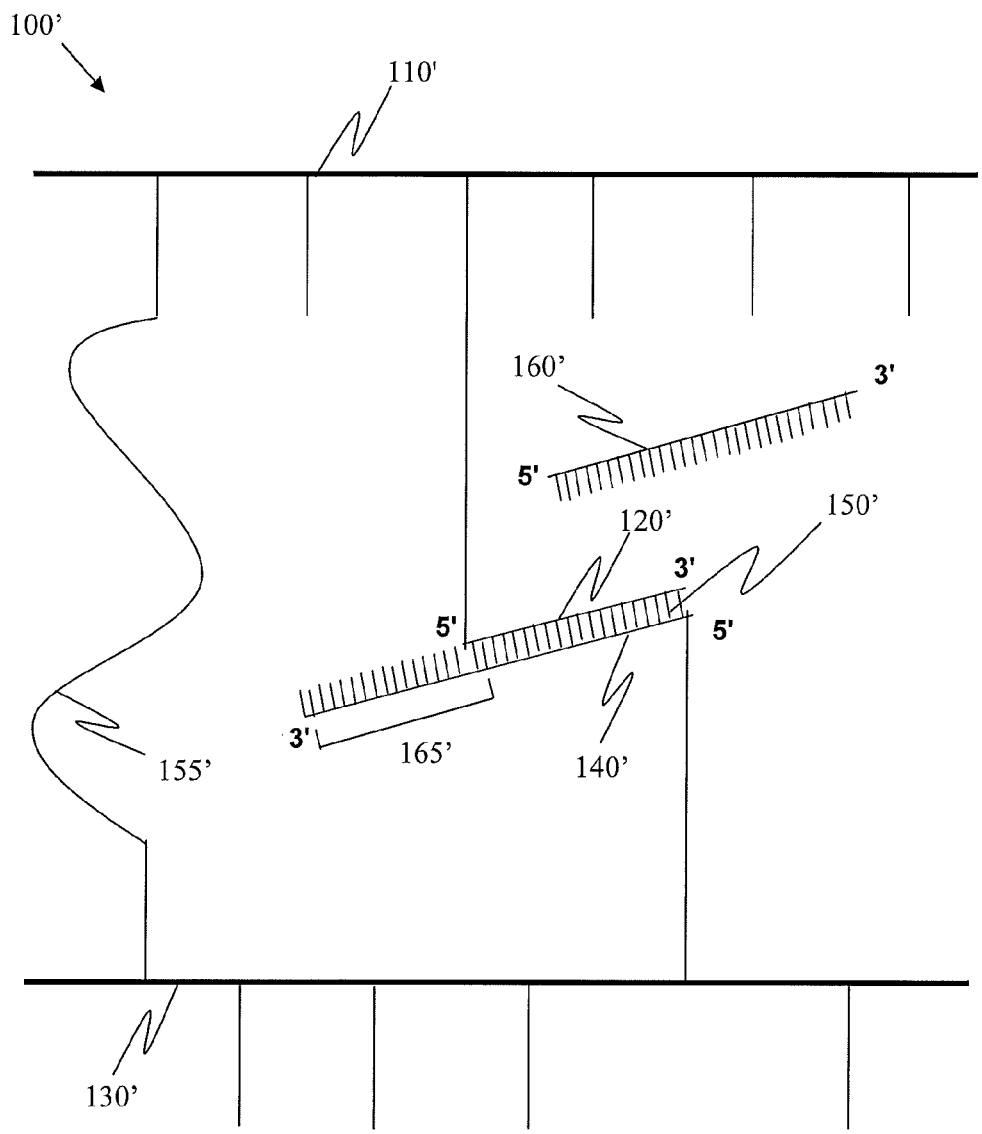
FIG. 1 schematically illustrates a detail view of a portion of a composition of the present invention.

Certain preferred embodiments of the present invention recognize the advantageous use of functional groups comprising nucleic acid sequences, attached as side-chains to polymers, to produce compositions. FIG. 1 illustrates a schematic representation of a portion of one such active agent delivery system 100. The composition 105 comprises a first polymer portion 110 having a first functional group comprising a nucleic acid sequence 120 attached as a side-chain thereto. The composition 105 further comprises a second polymer portion 130 having a second functional group comprising a nucleic acid sequence 140 attached as a side-chain thereto. The first and said second nucleic acid sequences 120, 140 are capable of forming a cross-link 150 between the first and second polymer portions 110, 130. The first and second polymer portions 110, 130 may comprise any polymer to which the nucleic acid sequences 120, 140 can be attached as side-chains thereto. The first and second polymer portions 110 may comprise a single polymer or comprise two or more separate polymers. Additionally, the first and second nucleic acid sequences 120, 140 may be distributed on the entire length of such polymer or polymers, or only on the first and second portions 110, 130.

An active agent 155 contained by the composition 105, is released by an interaction between an external substance 160 and the composition 105. The substance 160 may be a wide range of organic or inorganic compounds that are capable of breaking the cross-link 150. In a more specific embodiment, the substance 160 is capable of breaking hydrogen bonds between the first and second functional groups 120,140. Other examples of the substance 160 are also discussed below.

In certain preferred embodiments, the substance 160 is an enzyme capable of breaking the cross-link 150 by a cleavage of the first or said second functional groups 120, 140. The term enzyme as used herein, refers to any protein or ribozyme (i.e., molecular weight greater than about 1000 g/mole) capable of catalyzing the cleavage of the functional groups that crosslink the first and second polymer 110, 130. The enzyme may be naturally occurring or synthetically produced. In certain preferred embodiments, the enzyme is present in or released by an organism that is a target of the active agent. The organism may be an individual cell, such as a bacterium, a virus, or a collection of cells found in particular organs of higher animals, including man or domestic animals, or plants. The enzyme may be released from a cell selected from the group consisting of a cell in a digestive tract, for example the digestive tract of ruminants, or of a cell undergoing apoptosis, for example a cell following ischemia. Alternatively, the enzyme may be presented to the organism by artificial means, for example, via an injection of the enzyme itself, a precursor of the enzyme, or a second organism or other delivery system that releases the enzyme.

In certain embodiments, the enzyme may be a nuclease or a ribozyme. The term nuclease as used herein refers to any protein capable of promoting the cleavage of linkages in a nucleic acid sequence. The manner in which such cleavage occurs is well-know to those of ordinary skill in the art. Nucleases, for example, may cleave the phosphodiester bonds between nucleotide subunits of nucleic acids. Any of several classes of nucleases, such as endonucleases and exonucleases, may hydrolyze nucleic acids. In certain embodiments, for example, the nuclease may be selected from EC 3.1.11 to EC 3.1.31, using the nomenclature defined by the International Union of Biochemistry and Molecular Biology and published in Enzyme Nomenclature (1992) including Supplement 1 (1993), Supplement 2 (1994), Supplement 3 (1995), Supplement 4 (1997) and Supplement 5 (in Eur. J. Biochem. 1994, 223, 1-5; Eur. J. Biochem. 1995, 232, 1-6; Eur. J. Biochem. 1996, 237, 1-5; Eur. J. Biochem. 1997, 250; 1-6, and Eur. J. Biochem. 1999, 264, 610-650; respectively), all of which are incorporated herein by reference.

The term ribozyme as used herein refers to any nucleic acid sequence capable of promoting the cleavage of linkages in a nucleic acid sequence. Numerous classes of such nucleic acid sequences, such as ribonucleic acid (RNA), are well known to those of ordinary skill in the art. Non-limiting examples include Group I and II Introns, RNAase P, Hammerhead ribozymes, Hairpin ribozymes, Hepatitis Delta Virus produced ribozymes, or *Neurospora*-derived ribozymes.

In certain preferred embodiments, for example, when the first and second functional groups 120, 140 comprise single stranded nucleic acid sequences, the enzyme is capable of selectively cleaving a specific nucleic acid sequence in the first or second nucleic acid sequence 120, 140. For example, certain nucleases termed restriction endonuclease, commonly found in certain bacteria, recognize specific, short nucleotide sequences and cleave DNA at discreet locations in the sequence. In other preferred embodiments, the enzyme may comprise a first enzyme capable of selectively cleaving the first nucleic acid sequence 120 and a second enzyme capable of selectively cleaving the second nucleic acid sequence 140.

The release of the active agent 155 can be controlled by controlling the catalytic activity of the enzyme for the cleavage of the functional groups. For example, if the active agent 155 is to be released at a particular cell that produces a certain nuclease, then the particular order of base pairs in one or both of the first or second nucleic acid sequences 120, 140 can be selected such that the activity of the nuclease for the nucleic acid sequences is increased or decreased. Accordingly, the release of the active agent 155 from the composition 105 can be increased or decreased upon interaction of the nuclease with the composition 105.

Any of the embodiments of the composition 105 described in Mills may be used in the delivery system of the present invention to control the release of the active agent 155. In certain preferred embodiments, for example, the substance 160 is a third nucleic acid sequence 170, serving as a removal strand. In such embodiments, at least one of the first or second nucleic acid sequence 120, 140 further comprises a toe-hold nucleic acid sequence 165. The third nucleic acid sequence 170 is complementary to the toe-hold sequence 165 and the remainder of the first or second nucleic acid sequence 120, 140 comprising the toe hold sequence 165, so the third nucleic acid sequence 170 can bind at the toe-hold sequence 165 and thereby dissociate the cross-link 150. In certain preferred embodiments, the third nuclei acid sequence 170 is messenger RNA (mRNA). Thus, for example, the expression of a particular gene by a cell or organism embodied in mRNA production could cause the disassembly of the composition 105.

The active agent 155 may comprise any compound or group of compounds with structures that are contained by the composition 105. Preferably, the active agent 155 is a chemically active compound selected from the group consisting of: biochemical or chemical compounds, preferably with diagnostic or therapeutic properties, preferably suitable for identifying or therapeutically treating pathogens and toxins from biological fluid. Examples of suitable active agents include drugs, antibiotics or genes.

In certain embodiments, the active agent 155 may comprise a nucleic acid sequence released from the first or the second nucleic acid sequence 120, 140 by the interaction between a substance 160 comprising an enzyme and the composition 105.

Figure 2:
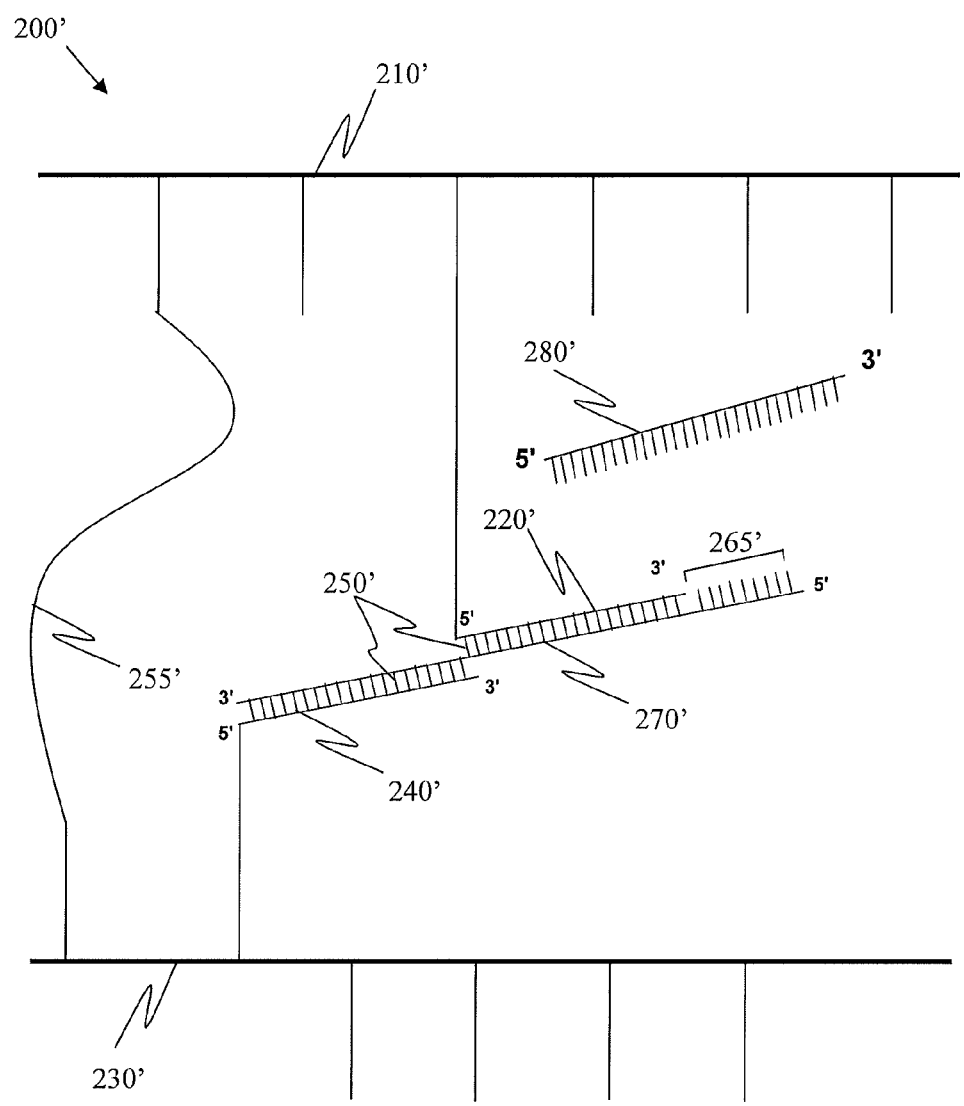
FIG. 2 schematically illustrates a detail view of a portion of an alternative composition of the present invention.
Figure 3:
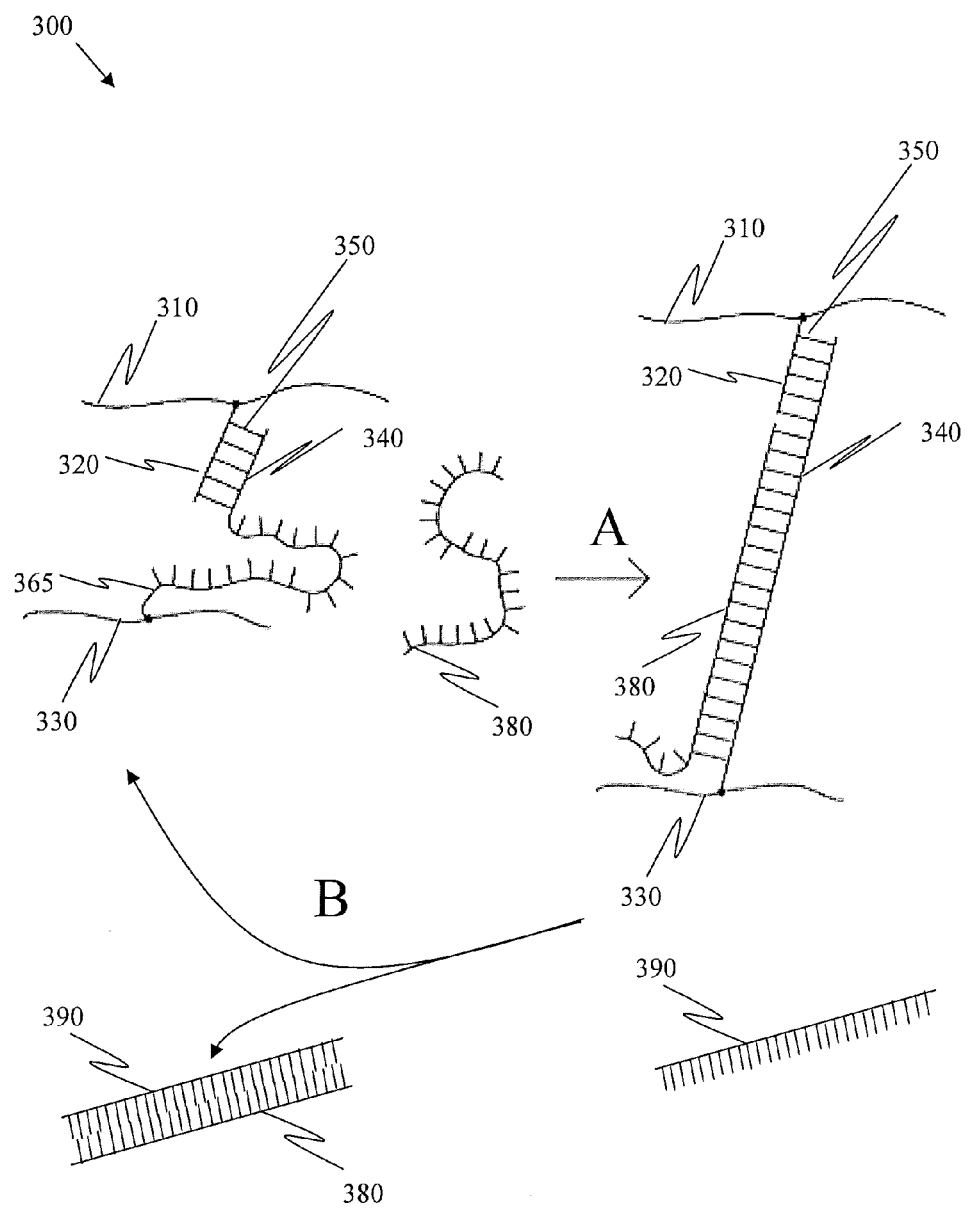
FIG. 3 schematically illustrates the swelling and shrinkage of a gel composition according to the present invention.
Figure 4:
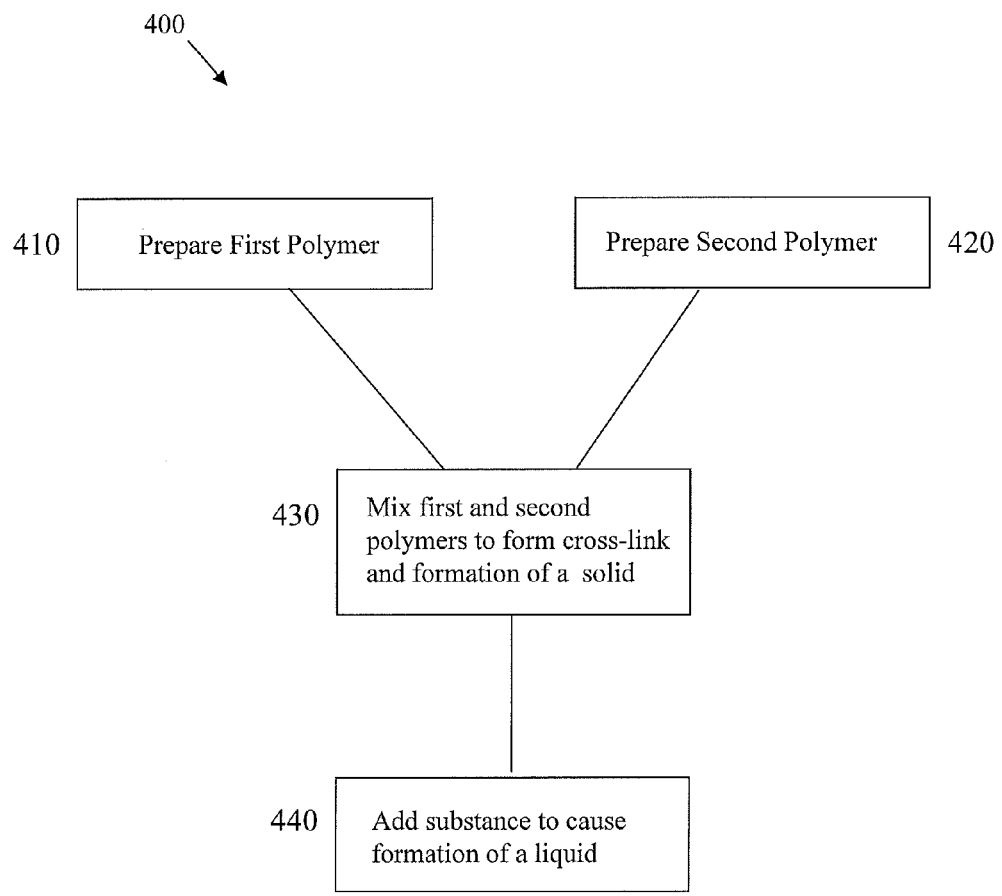
FIG. 4 illustrates, by flow diagram, a method for making a composition of the present invention.
Figure 5:
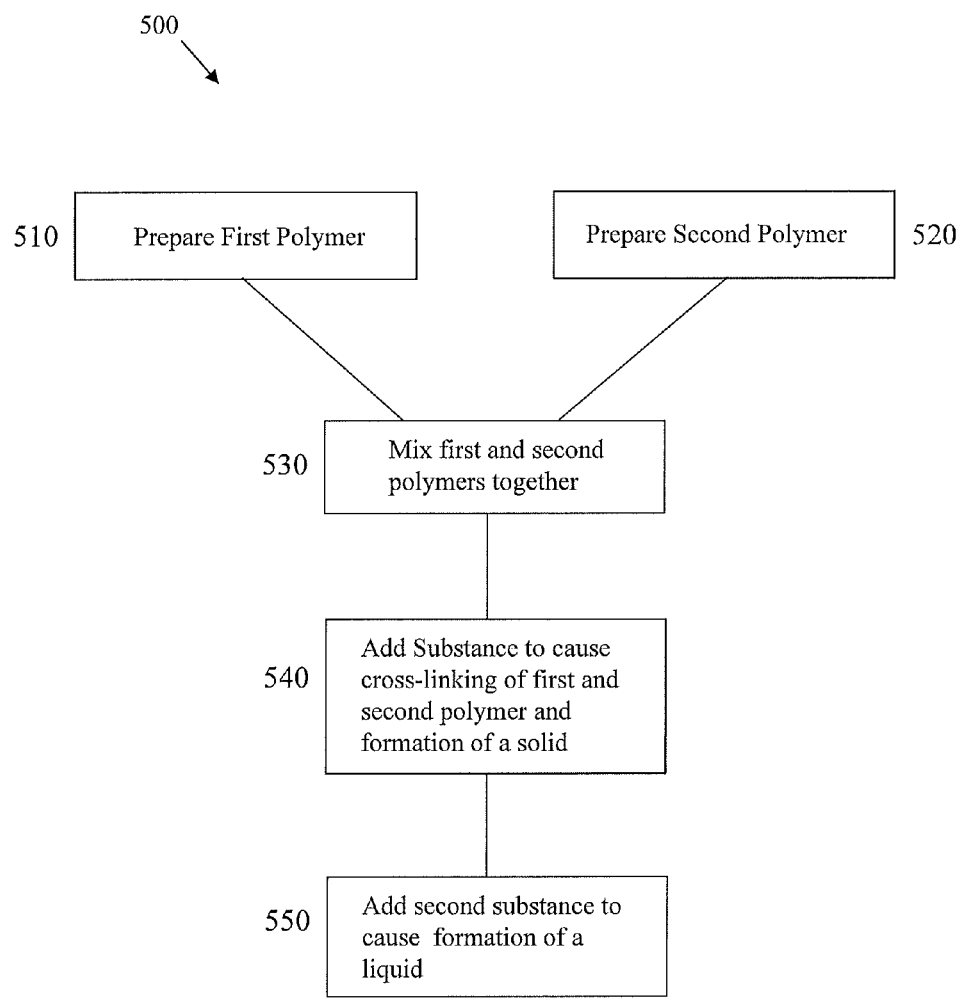
FIG. 5 illustrates, by flow diagram, a second method for making a composition of the present invention.
Figure 6:
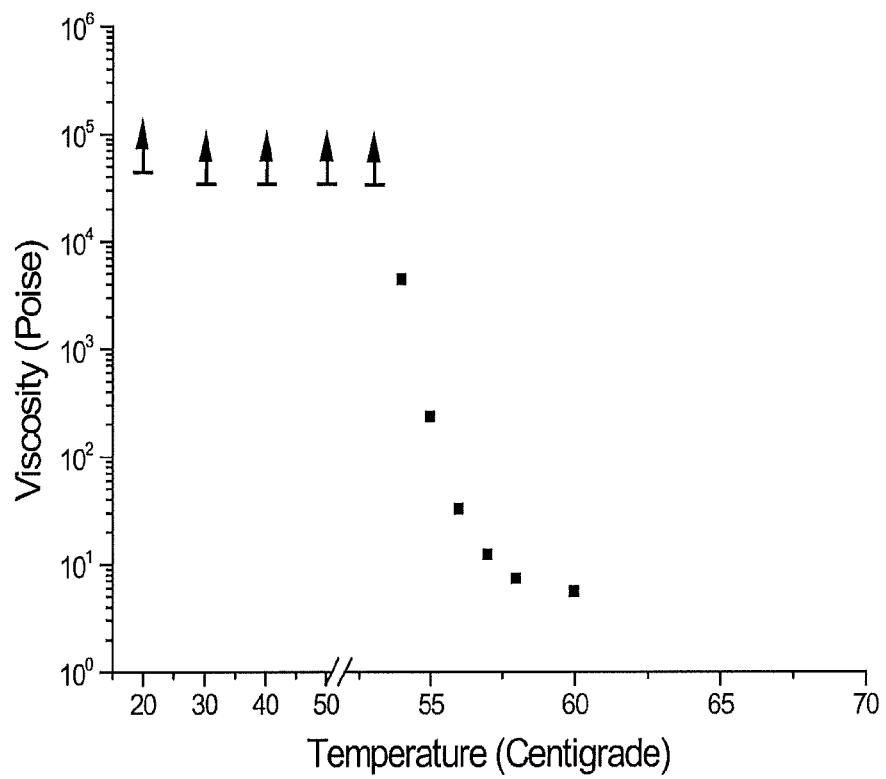
FIG. 6 illustrates the relationship between temperature and viscosity for a representative composition of the present invention.
Figure 7:
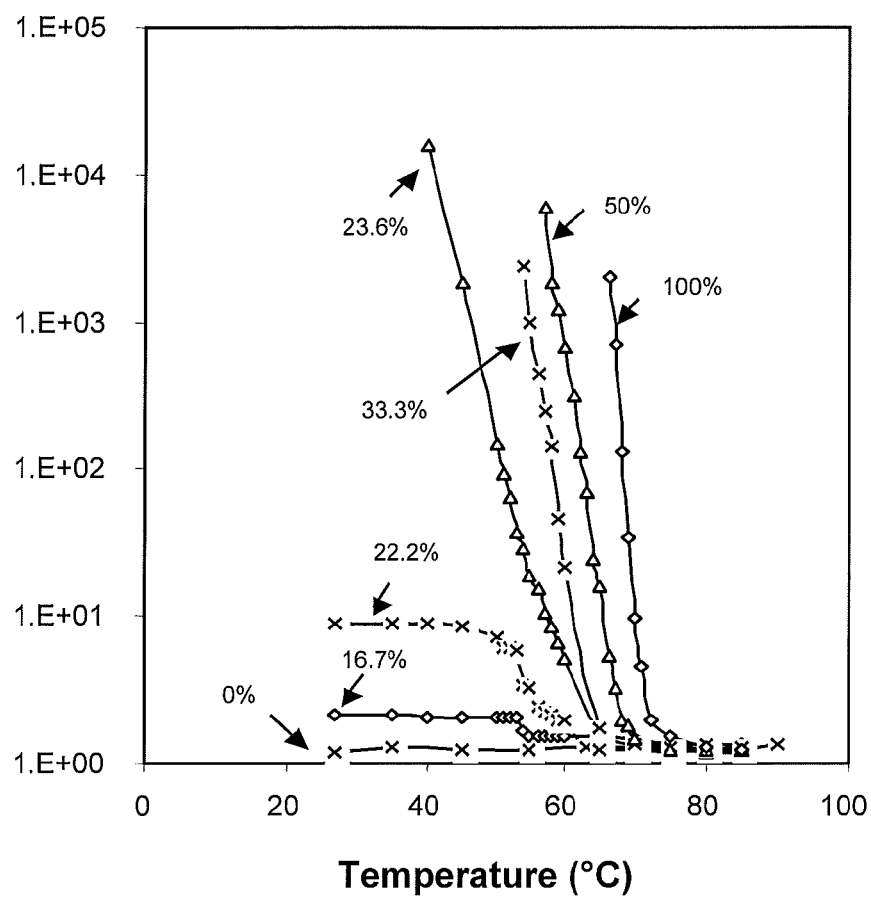
FIG. 7 illustrates the relationship between temperature and viscosity for representative compositions of the present invention having different amounts of a nucleic acid sequence serving as a cross-linker.
Figure 8:
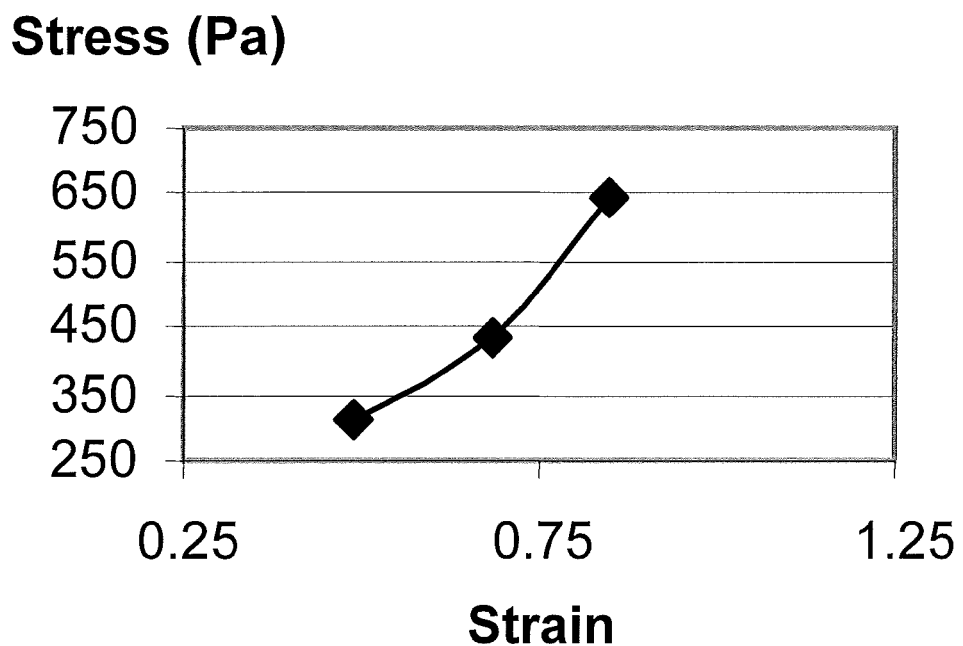
FIG. 8 illustrate the stress-strain relationship for a representative composition of the present invention.
Figure 9:
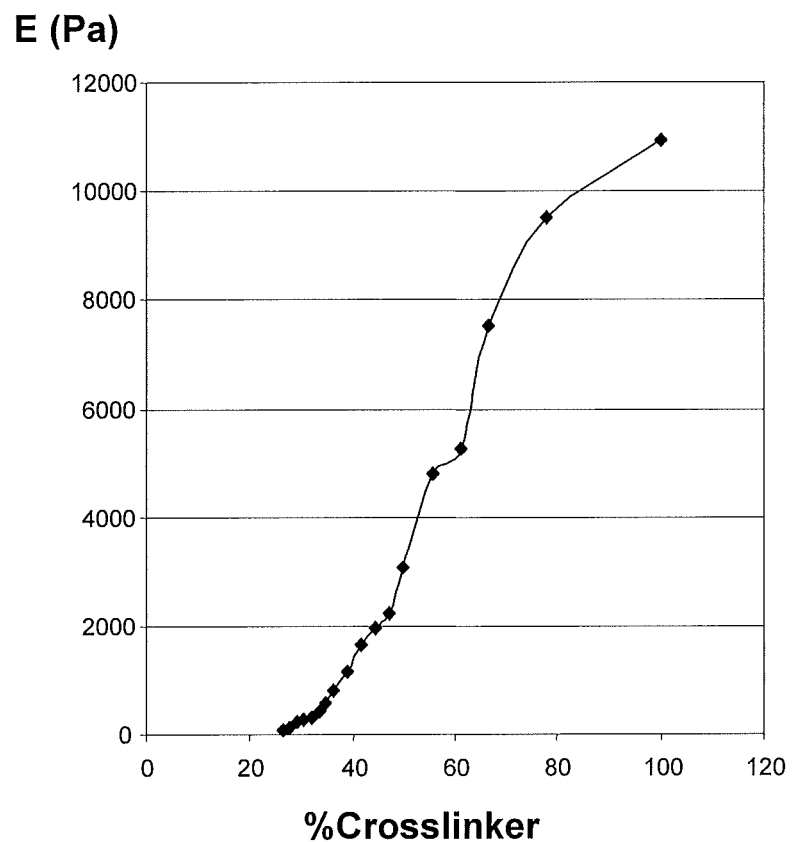
FIG. 9 illustrates the change in elastic modulus for representative compositions of the present invention having different amounts of a linking nucleic acid sequence.

In alternative preferred embodiments of the delivery system 200, as illustrated in FIG. 2, where like reference numbers refer to like elements shown in FIG. 1, the composition 205 may further include a third nucleic acid sequence 280, serving as a linking strand. The third sequence attaches to the first and to the second nucleic acid sequences 220, 240 to facilitate formation of the cross-link 250. In turn, the cross-link 250 is capable of being broken by a cleavage of the third nucleic acid sequence 280 by a substance 260 comprising an enzyme. Alternatively the substance 260 may comprise a fourth nucleic acid sequence 270.

Analogous to that described above for the system 100 presented in FIG. 1, the fourth nucleic acid sequence 270 is complementary to a toe-hold 285 nucleic acid sequence and the remainder of the third nucleic acid sequence 280. Thus, binding of the fourth nucleic acid sequence 280 causes dissociation of the cross-link 250. Thus, the fourth sequence 280 serves as a removal strand.

Another embodiment of the present invention is a method for delivering an active agent to an organism. The method includes introducing a composition into an organism. The composition comprises a first polymer portion having first functional groups attached as a side-chain thereto and a second polymer portion having second functional groups attached as a side-chain thereto. An active agent is disposed between the polymer portions, the first and the second functional groups forming a cross-link between the first and the second polymer portions. The organism includes a substance capable of releasing the active agent from the composition by breaking the cross-links.

In certain preferred embodiments, the method for the delivering an active agent to an organism can be targeted to particular cells in the organism, for example, because the substance is an enzyme that is produced in or released by cells in the organism that are a target for presentation of the active agent thereto. For instance, the enzyme may be released from a cell selected from a cell in a digestive tract or a cell undergoing apoptosis.

In certain preferred embodiments, the release of the active agent is a function of a catalytic activity of the enzyme for the cleavage of the first and second functional groups. In turn, the catalytic activity of the enzyme for cleavage of the nucleic acid sequences can be controlled by selecting particular nucleic acid sequences used for cross-linking. Knowledge of the specificity of the enzyme produced in or released by the target cells, for example, would allow the selection of a nucleic acid sequence that is more or less readily cleaved by the enzyme. Thus, in certain embodiments, the enzyme is capable of selectively cleaving a specific nucleic acid sequence in the first nucleic acid sequence or the second nucleic acid sequence. Alternatively, there may be a first enzyme that selectively cleaves the first nucleic acid sequence and a second enzyme that selectively cleaves the second nucleic acid sequence.

Releasing the active agent may be achieved by interacting the composition with a substance comprising a third polymer having a third functional group, such as a nucleic acid sequence, attached as a side-chain thereto. In such embodiments, one of the first or second nucleic acid sequences has a toe-hold sequence sufficiently complementary to the third sequence that the latter facilitates dissociation of the cross-link.

Alternatively, as noted in Mills and elsewhere herein, the third polymer has third functional groups attached as chains thereto. For example, a third nucleic acid sequence serves as a linking strand by attaching to the first and the second nucleic acid sequences to form the cross-link. In such embodiments, cross-link may be broken by a cleavage of said third nucleic acid sequence by a substance that is one of the target organism's enzymes. Alternatively, the release of the active agent in such embodiments can be achieved by a substance that acts as a removal strand. For the substance may be a fourth nucleic acid sequence such as discussed above. In such embodiments, the third nucleic acid sequence includes a toe-hold sequence complementary to a portion of the removal strand.

Although the present invention has been described in detail, those of ordinary skill in the art should understand that they can make various changes, substitutions and alterations herein without departing from the scope of the invention.

What is claimed is:

1. A method for delivering an active agent to an organism, comprising:
   introducing a composition into an organism, said composition comprising:
   a gel formed from:
   first polymers having first functional groups comprising a first nucleic acid sequence attached as side-chains thereto; and
   second polymers having second functional groups comprising a second nucleic acid sequence attached as side-chains thereto, said first and said second functional groups form reversible cross-links between said first and said second polymers, wherein said cross links comprise a plurality of hydrogen bonds between complementary base portions of said first and said second nucleic acid sequences; and
   further including therein said gel an active agent disposed between said first and second polymers, said active agent capable of being released by an interaction of a substance with said first or said second nucleic acid sequences to thereby break said cross-links, wherein:

said first and second polymers are separate polymers and said first and second polymers are held together by said hydrogen bonds, said gel is in a solid state when said cross-links are unbroken, and said gel is in a fluid state when said cross-links are broken, and wherein said organism includes a substance capable of releasing said active agent from said composition by breaking said cross-links.

2. The method of claim 1 wherein said substance is produced or released by cells in said organism.

3. The method of claim 1, wherein said substance is an enzyme capable of cleaving said first or said second functional groups.

4. The method of claim 3, wherein said enzyme is selected from the group consisting of nucleases and ribozymes.

5. The method of claim 3 wherein said substance includes a third nucleic acid sequence and at least one of said first nucleic acid sequence or said second nucleic acid sequence further comprise a nucleic acid sequence, wherein said third nucleic acid sequence is sufficiently complementary to a portion of said nucleic acid sequence such that said third nucleic acid sequence causes a dissociation of said cross links.

6. The method of claim 1, wherein said composition further includes a third nucleic acid sequence capable of attaching to said first and said second nucleic acid sequences to facilitate formation of said cross links.

7. The method of claim 6, wherein said substance includes a fourth nucleic acid sequence and said third nucleic acid sequence comprises a nucleic acid sequence, wherein said fourth nucleic acid sequence is sufficiently complementary to said nucleic acid sequence to cause a dissociation of said cross links.

8. The method of claim 1, wherein said active agent includes a protein.

9. The method of claim 1, wherein said active agent includes a nucleic acid sequence.

10. The method of claim 1, wherein said active agent includes a nucleic acid sequence released from said first or said second nucleic acid sequence.

11. The method of claim 1, wherein said active agent includes drugs.

12. The method of claim 1, wherein said includes antibiotics.

* * * * *